US011172899B2

(12) United States Patent
Shimazu et al.

(10) Patent No.: US 11,172,899 B2
(45) Date of Patent: Nov. 16, 2021

(54) X-RAY FLUOROSCOPIC IMAGING APPARATUS

(71) Applicant: Shimadzu Corporation, Kyoto (JP)

(72) Inventors: Keisuke Shimazu, Kyoto (JP); Shinsuke Kanazawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 69 days.

(21) Appl. No.: 16/572,970

(22) Filed: Sep. 17, 2019

(65) Prior Publication Data
US 2020/0383653 A1    Dec. 10, 2020

(30) Foreign Application Priority Data

Jun. 5, 2019   (JP) .............................. JP2019-105362

(51) Int. Cl.
*A61B 6/02* (2006.01)
*G01N 23/04* (2018.01)
*A61B 6/00* (2006.01)

(52) U.S. Cl.
CPC .............. *A61B 6/487* (2013.01); *A61B 6/467* (2013.01)

(58) Field of Classification Search
CPC ........ G16H 20/40; G16H 40/60; G16H 40/63; G16H 50/20; G16H 70/20; A61B 6/467; A61B 6/487; A61B 6/4014; A61B 6/4405; A61B 6/4441; A61B 6/463; A61B 17/3468; A61B 6/4266; A61B 6/4482; A61B 6/542; A61B 6/545; A61B 6/56; A61B 17/22032; A61B 17/221; A61B 17/32056; A61B 17/320725; A61B 17/3403; A61B 2017/22034; A61B 2017/22061; A61B 2017/22082; A61B 17/7086; A61B 18/24; A61B 2017/0256; A61B 18/1492; A61B 2018/00214; A61B 2018/00351; A61B 2017/00084; A61B 2017/00243; A61B 2018/00666; A61B 2018/00898; A61B 2018/1467; A61B 2018/1475; A61B 18/02; A61B 2018/0016; A61B 2018/00577; A61B 2018/00642; A61B 2018/00654; A61B 2018/00702; A61B 6/465; A61B 6/5205; A61B 6/025; A61B 6/5223; A61B 6/54; A61B 6/4452; A61B 6/461; A61B 6/50; A61B 6/5258; A61B 6/563;

(Continued)

(56) References Cited

U.S. PATENT DOCUMENTS

2012/0014513 A1* 1/2012 Watanabe .............. A61B 5/055
378/209
2013/0272499 A1* 10/2013 Simmons ............... A61B 6/487
378/62

(Continued)

FOREIGN PATENT DOCUMENTS

JP    2000-166905 A    6/2000

*Primary Examiner* — Irakli Kiknadze
(74) *Attorney, Agent, or Firm* — Muir Patent Law, PLLC

(57) ABSTRACT

The X-ray fluoroscopic imaging apparatus is provided with an imaging unit including an X-ray source and an X-ray detector, a handle, a fluoroscopic button, and an imaging button. At least one of a fluoroscopic button and an imaging button is composed of a plurality of buttons provided on at least one end portion side in a direction along which the handle extends, and the plurality of buttons is mutually offset in a direction intersecting with the direction along which the handle extends.

8 Claims, 7 Drawing Sheets

(58) Field of Classification Search
CPC ......... A61B 6/032; A61B 6/04; A61B 6/0407;
A61B 6/4085; G01N 23/043
USPC .............................................. 378/42, 44, 62
See application file for complete search history.

(56) References Cited

U.S. PATENT DOCUMENTS

2014/0050304 A1* 2/2014 Florent .................. A61B 6/461
378/62
2016/0135760 A1* 5/2016 Miyazawa ........... A61B 6/4452
378/25

* cited by examiner

X-RAY FLUOROSCOPIC IMAGING APPARATUS

CROSS-REFERENCE TO THE RELATED APPLICATIONS

The priority application number JP2019-105362, entitled "X-ray fluoroscopic imaging apparatus", filed on Jun. 5, 2019 (publication date: Nov. 25, 2018), invented by Keisuke Shimazu, and Shinsuke Kanazawa upon which this patent application is based are hereby incorporated by reference.

BACKGROUND OF THE INVENTION

Field of the Invention

The present invention relates to an X-ray fluoroscopic imaging apparatus.

Description of the Background Art

Conventionally, an X-ray fluoroscopic imaging apparatus is known. Such an X-ray fluoroscopic imaging apparatus is disclosed in, for example, Japanese Unexamined Patent Application Publication No. 2000-166905.

Japanese Unexamined Patent Application Publication No. 2000-166905 discloses an X-ray fluoroscopic imaging apparatus provided with an X-ray tube for emitting X-rays to a subject, an X-ray imaging system for imaging X-rays transmitted through the subject, a top board configured to place the subject thereon, and an operation handle gripped by an inspector who operates the X-ray imaging system, and an imaging switch for executing imaging. In the X-ray fluoroscopic imaging apparatus disclosed in Japanese Unexamined Patent Application Publication No. 2000-166905, imaging is executed by pushing the imaging switch at the region of interest while moving the X-ray imaging system with the operation handle gripped by the inspector. The operation handle is configured to be able to move the X-ray imaging system in the vertical direction or the horizontal direction, and is provided with an operation switch in the vicinity of the operation handle.

In the X-ray fluoroscopic imaging apparatus disclosed in Japanese Unexamined Patent Application Publication No. 2000-166905, imaging is executed by pushing the imaging switch (button) in the region of interest while moving the X-ray imaging system with the operation handle gripped by the inspector (operator). Further, the operation handle is configured to be able to move the X-ray imaging system (imaging unit) in the vertical direction or the horizontal direction, and is provided with an imaging switch (button) in the vicinity of the operation handle.

In the X-ray fluoroscopic imaging apparatus as disclosed by, e.g., Japanese Unexamined Patent Application Publication No 2000-166905, the gripping position when the operator grips the handle differs depending on the height position of the handle. As a result, the position of the fingertip relative to the handle when the operator grips the handle changes depending on the height position of the handle. For this reason, depending on the gripping position, the distance between the position of the fingertip and the button increases. As a result, depending on the position of the handle, in some cases, it is difficult for the operator to perform the button operation while performing the operation of moving the imaging unit in a state in which the operator grips the handle. Under the circumstance, it has been desired to provide an X-ray fluoroscopic imaging apparatus capable of easily performing a button operation while performing an operation of moving an imaging unit regardless of a position of a handle.

The present invention has been made to solve the aforementioned problems, and one object of the present invention is to provide an X-ray fluoroscopic imaging apparatus capable of easily performing a button operation while performing an operation of moving an imaging unit regardless of a position of a handle.

SUMMARY OF THE INVENTION

In order to attain the aforementioned object, an X-ray fluoroscopic imaging apparatus according to one aspect of the present invention includes:

a top board configured to place a subject thereon;

an imaging unit including an X-ray source configured to emit X-rays toward the subject and an X-ray detector configured to detect X-rays emitted from the X-ray source and transmitted through the subject;

an image processing unit configured to generate an X-ray fluoroscopic image and an X-ray image based on a detection signal acquired by the imaging unit;

a handle configured to be gripped by an operator when relatively moving the imaging unit relative to the top board at least in a horizontal direction or vertical direction;

a fluoroscopic button configured to perform an instruction to execute X-ray fluoroscopy; and an imaging button configured to perform an instruction to execute X-ray imaging with an X-ray dose more than an X-ray dose used when executing the X-ray fluoroscopy, wherein at least one of the fluoroscopic button and the imaging button is configured to be able to perform an instruction operation in a state in which the operator grips the handle, and is composed of a plurality of buttons arranged at least on one end portion side in a direction along which the handle extends and arranged offset in a direction intersecting with the direction along which the handle extends.

According to the present invention, at least one of the fluoroscopic button and the imaging button is configured to be able to perform an instruction operation in a state in which the operator grips the handle, and is composed of a plurality of buttons provided at least on one end portion side in a direction along which the handle extends and arranged offset in a direction intersecting with the direction along which the handles extend. This makes it possible to provide the button at a position where it is easy to be operated in a plurality of gripping positions. As a result, the button operation can be easily performed while performing the moving operation of the imaging unit regardless of the position of the handle.

DESCRIPTION OF PREFERRED EMBODIMENTS

Hereinafter, embodiments embodying the present invention will be described with reference to the drawings.

Configuration of X-Ray Fluoroscopic Imaging Apparatus

Figure 1:
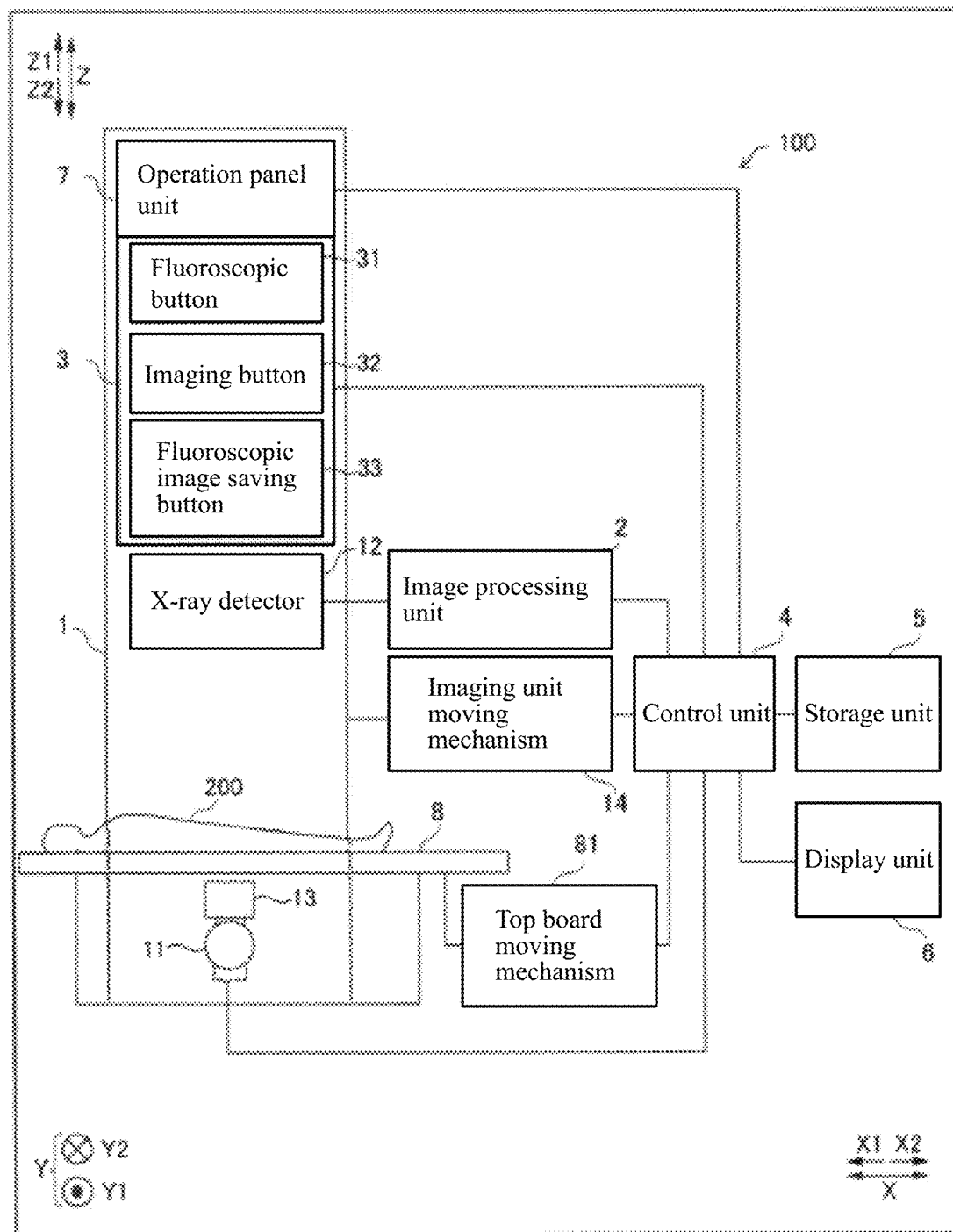
FIG. 1 is a block diagram showing an overall configuration of an X-ray fluoroscopic imaging apparatus according to one embodiment of the present invention.

As shown in FIG. 1, the X-ray fluoroscopic imaging apparatus 100 of this embodiment is provided with an imaging unit 1, an image processing unit 2, a handle 3, a control unit 4, a storage unit 5, a display unit 6, an operation panel unit 7, and a top board 8. Further, in the example shown in FIG. 1, the imaging unit 1 is connected to an imaging unit moving mechanism 14, and the top board 8 is connected to a top board moving mechanism 81.

The top board 8 is configured to place a subject 200 thereon. The top board 8 is formed in a rectangular flat plate shape in a plan view. The subject 200 is placed on the top board 8 so that the longitudinal direction of the subject 200 is a direction along the long side of the rectangle and the left-right direction of the subject 200 is a direction along the short side of the rectangle.

In this specification, the vertical direction is defined as a Z-direction, the upward direction is defined as a Z1-direction, and the downward direction is defined as a Z2-direction. Further, two directions orthogonal to each other in the horizontal direction are defined as an X-direction and a Y-direction. One of the X-direction is defined as an X1-direction and the other is defined as an X2-direction. One of the Y-direction is defined as a Y1-direction and the other is defined as a Y2-direction. In the example shown in FIG. 1, the subject 200 is placed so that the head of the subject 200 is directed in the X1-direction. Note that the longitudinal direction of the subject 200 denotes a direction along a straight line connecting the head and the foot of the subject 200. That is, when the top board 8 is in the horizontal state, the X-direction is the longitudinal direction of the top board 8. Further, when the top board 8 is in the horizontal state, the Y-direction is the short direction of the top board 8.

The imaging unit 1 includes an X-ray source 11, an X-ray detector 12, a collimator 13, a handle 3, and an operation panel unit 7. The imaging unit 1 is configured to execute X-ray imaging and X-ray fluoroscopy by detecting X-rays emitted from the X-ray source 11 to the subject 200 with the X-ray detector 12. The X-ray source 11 is configured to emit X-rays toward the subject 200 when a voltage is applied by an X-ray tube drive unit (not shown). The X-ray source 11 and the X-ray detector 12 are provided at mutually opposing positions across the top board 8.

The collimator 13 is arranged between the X-ray source 11 and the X-ray detector 12. The collimator 13 is configured to be able to shield X-rays. The collimator 13 is configured to be able to adjust the X-ray irradiation range by shielding a part of the X-rays emitted from the X-ray source 11. The collimator 13 contains heavy metals, such as, e.g., lead, gold, and tungsten.

The X-ray detector 12 is configured to detect X-rays emitted from the X-ray source 11 and transmitted through the subject 200. The X-ray detector 12 includes, for example, an FPD (Flat Panel Detector) or an II (Image Intensifier). The X-ray detector 12 is configured by a plurality of conversion elements (not shown) and a plurality of pixel electrodes (not shown) arranged on the plurality of conversion elements. The plurality of conversion elements and pixel electrodes are arranged in an array on the detection surface at a predetermined cycle (pixel pitch). Further, the X-ray detector 12 is configured to output the acquired image signal to the image processing unit 2.

The image processing unit 2 is configured to generate an X-ray fluoroscopic image based on the image information acquired by the imaging unit 1. Specifically, the image processing unit 2 is configured to generate an X-ray fluoroscopic image as a moving image. The X-ray fluoroscopic image generated by the image processing unit 2 is displayed on the display unit 6. Therefore, the operator 201 can change the imaging position and/or change the X-ray irradiation range in real time while confirming the X-ray fluoroscopic image generated by the image processing unit 2. The image processing unit 2 includes a processor, such as, e.g., a GPU (Graphics Processing Unit) and an FPGA (Field-Programmable Gate Array) configured for image processing.

The handle 3 is gripped when the operator 201 (see FIG. 2 and FIG. 3) moves the imaging unit 1. That is, while gripping the handle 3, the operator 201 relatively moves the imaging unit 1 relative to the top board 8 in the horizontal direction or the vertical direction by applying a force in a direction along which the imaging unit 1 is to be moved. The handle 3 extends along a direction (X-direction) substantially parallel to the operation panel unit 7, and is attached to the operation panel unit 7. The handle 3 is made of, for example, resin. The handle 3 is provided with a fluoroscopic button 31, an imaging button 32, and a fluoroscopic image saving button 33 as described later. The operator 201 operates these buttons while relatively moving the imaging unit 1 relative to the top board 8 in the horizontal direction or the vertical direction. Further, these buttons (the fluoroscopic button 31, the imaging button 32, and the fluoroscopic image saving button 33) can be operated with a finger in a state in which the operator 201 grips the handle 3. Note that a finger described in this specification includes a thumb, a forefinger, a middle finger, a ring finger, and a little finger.

The control unit 4 is configured to control the imaging unit moving mechanism 14 to perform power assist when the operator 201 moves the imaging unit 1. Further, the control unit 4 is configured to control the top board moving mechanism 81 to relatively move the top board 8 and the imaging unit 1. Further, the control unit 4 is configured to control the collimator 13 to adjust the X-ray irradiation range. The control unit 4 is a computer configured so as to include a CPU (Central Processing Unit), a ROM (Read Only Memory), a RAM (Random Access Memory), and the like. Further, the control unit 4 is configured to receive operations from the handle 3 and the operation panel unit 7 described later, and perform various controls.

The storage unit 5 includes, for example, an HDD (hard disk drive) or a nonvolatile memory. The storage unit 5 is configured to store image information acquired by the imaging unit 1, the X-ray image and the X-ray fluoroscopic image, etc., generated by the image processing unit 2. The X-ray fluoroscopic image for X-ray fluoroscopy is stored as a moving image in the storage unit 5.

The display unit 6 is configured as, for example, a liquid crystal display. The display unit 6 is configured to display the X-ray fluoroscopic image generated by the image processing unit 2 based on the image information acquired by the imaging unit 1.

The operation panel unit 7 is integrally provided to the imaging unit 1. Further, the operation panel unit 7 receives an operation input for operating the imaging unit 1.

The imaging unit moving mechanism 14 movably holds the imaging unit 1. The imaging unit moving mechanism 14 is configured to move the imaging unit 1 in the direction of the force applied by the operator 201 to the handle 3 under the control of the control unit 4. The imaging unit moving mechanism 14 functions as a power assist mechanism, for example, when the operator 201 moves the imaging unit 1. Further, when the imaging unit 1 is operated by the operation panel unit 7 or operated (remotely operated) by a console (not shown) provided at a position different from the X-ray fluoroscopic imaging apparatus 100, the imaging unit moving mechanism 14 functions as a moving mechanism for moving the imaging unit 1 based on the input signal from the operation panel unit 7 or the control of the control unit 4 (not shown) of the console.

The imaging unit moving mechanism 14 includes a linear motion mechanism movable in each of the X-direction, the Y-direction, and the Z-direction, and is configured to be able to move the imaging unit 1 in each direction. The imaging unit moving mechanism 14 includes a linear motion mechanism capable of move the X-ray source 11 in the X-direction and Y-direction, and is configured to be able to move the X-ray source 11 in the X-direction and Y-direction. The linear motion mechanism in each direction included in the imaging unit moving mechanism 14 is, for example, a belt-pulley mechanism including a drive motor (not shown), a pair of rollers (not shown), and a timing belt (not shown).

The top board moving mechanism 81 is configured to move the top board 8 to change the relative position of the top board 8 with respect to the imaging unit 1 under the control of the control unit 4. Specifically, the top board moving mechanism 81 is configured to be able to change the relative position of the top board 8 and the imaging unit 1 by moving the top board 8 in the X-direction and the Y-direction. The top board moving mechanism 81 includes a linear motion mechanism movable in the X-direction and Y-direction. The linear motion mechanism in each direction included in the top board moving mechanism 81 is, for example, a belt-pulley mechanism including a drive motor (not shown), a pair of rollers (not shown), and a timing belt (not shown).

Adjustment of Imaging Unit When X-Ray Imaging

Figure 2:
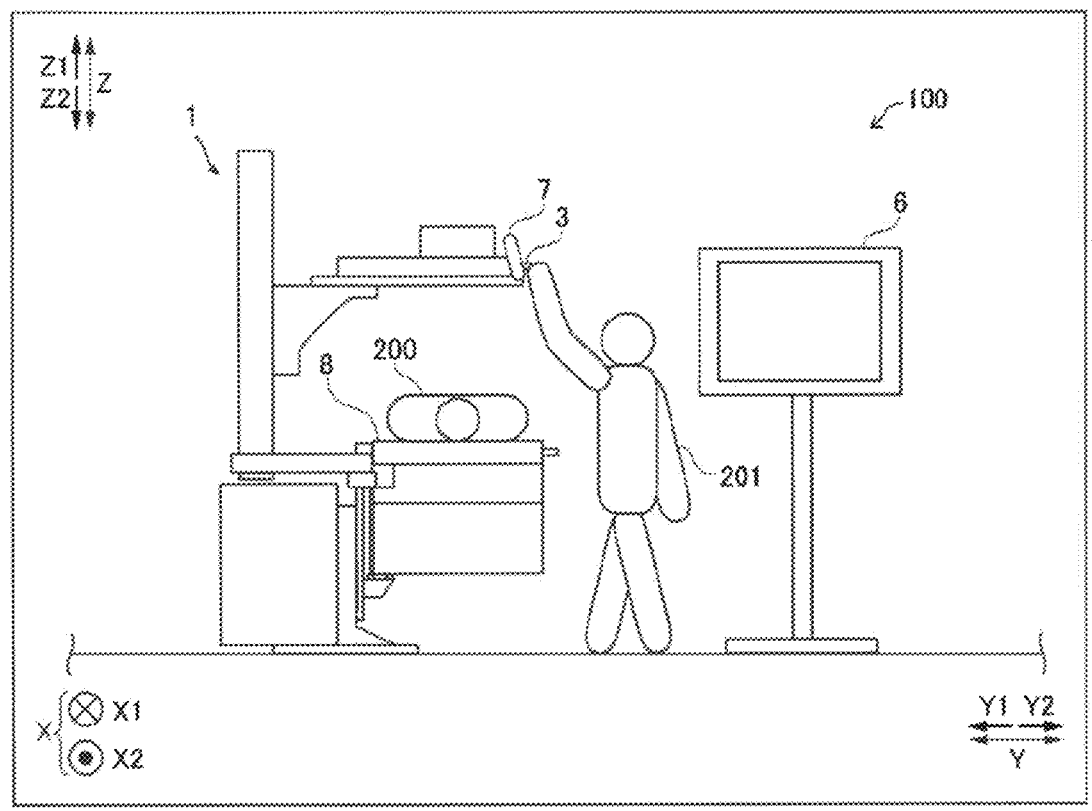
FIG. 2 is a schematic diagram showing the overall configuration of the X-ray fluoroscopic imaging apparatus according to the embodiment of the present invention.

The X-ray fluoroscopic imaging apparatus 100 is configured so that an X-ray fluoroscopic image and an X-ray image can be obtained in two ways, X-ray fluoroscopy and X-ray imaging. In the X-ray fluoroscopy, since a radiation dose smaller than that in the X-ray imaging is irradiated to the subject 200, the exposure dose of the subject 200 can be reduced, but a low-quality image (X-ray fluoroscopic image) is acquired. On the other hand, in the X-ray imaging, an image (X-ray image) having a certain degree of high image quality is acquired. As shown in FIG. 2, when executing X-ray imaging and X-ray fluoroscopy, the operator 201 moves the imaging unit 1 and adjusts the irradiation range of X-rays in a state in which the subject 200 is placed on the top board 8.

Specifically, the operator 201 performs the X-ray fluoroscopy of the subject 200 while moving the imaging unit 1 in the state in which the handle 3 is gripped. Further, the operator 201 adjusts the X-ray irradiation range so that the range becomes suitable for the region of interest as the imaging unit 1 moves. The movement of the imaging unit 1 and the adjustment of the X-ray irradiation range are performed while the operator 201 is looking at the X-ray fluoroscopic image displayed on the display unit 6. The operator 201 operates the buttons provided on the operation panel unit 7 or the handle 3 while moving the imaging unit 1 to repeatedly perform the adjustment of the X-ray irradiation range and the X-ray imaging to image a predetermined region of interest. The captured X-ray image is stored in the storage unit 5. Further, the X-ray fluoroscopic image at the time of the X-ray fluoroscopy is stored as a moving image in the storage unit 5.

Figure 3:
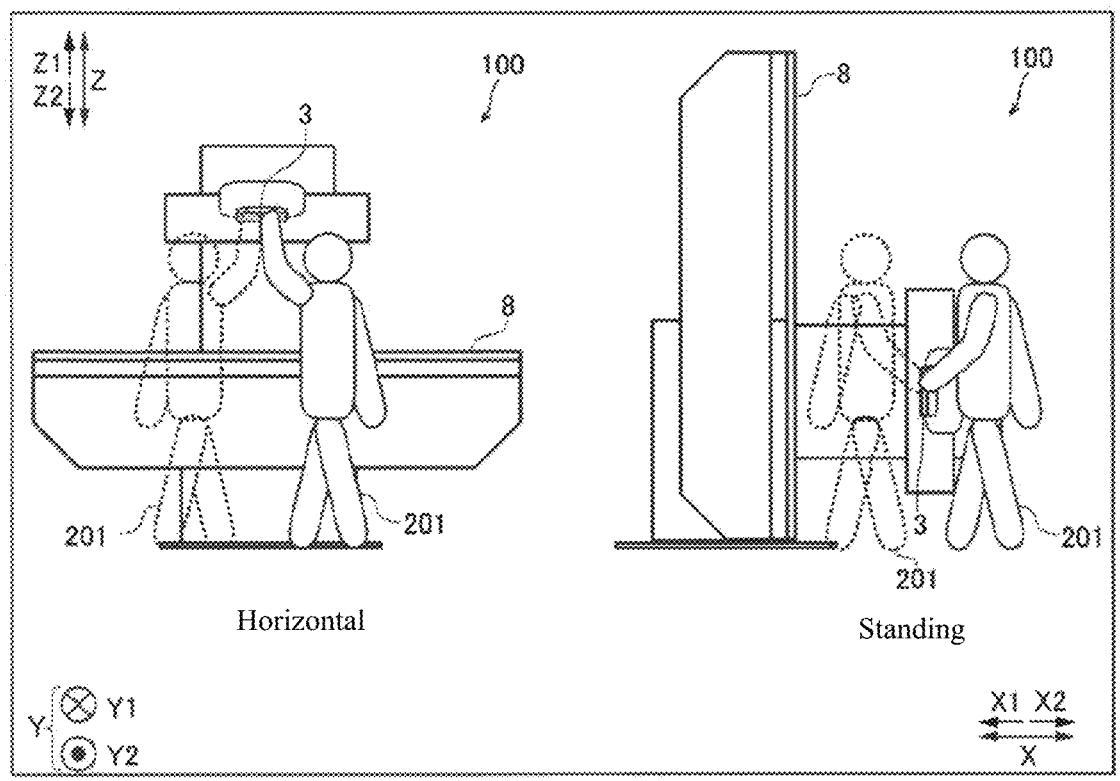
FIG. 3 is a schematic diagram showing an example of a handle position and a gripping state by an operator in a horizontal state and a standing state of the X-ray fluoroscopic imaging apparatus according the embodiment of the present invention.

The X-ray fluoroscopic imaging apparatus 100 of this embodiment can execute X-ray fluoroscopy and X-ray imaging in a state in which the top board 8 (the posture of the apparatus) is in a horizontal state and in a standing state as shown in FIG. 3. Depending on the posture (horizontal state and standing state) of the X-ray fluoroscopic imaging apparatus 100, the position of the operator 201, and the gripping hand, the gripping position of the handle 3 changes according to the situation.

Operation Panel Unit

Figure 4:
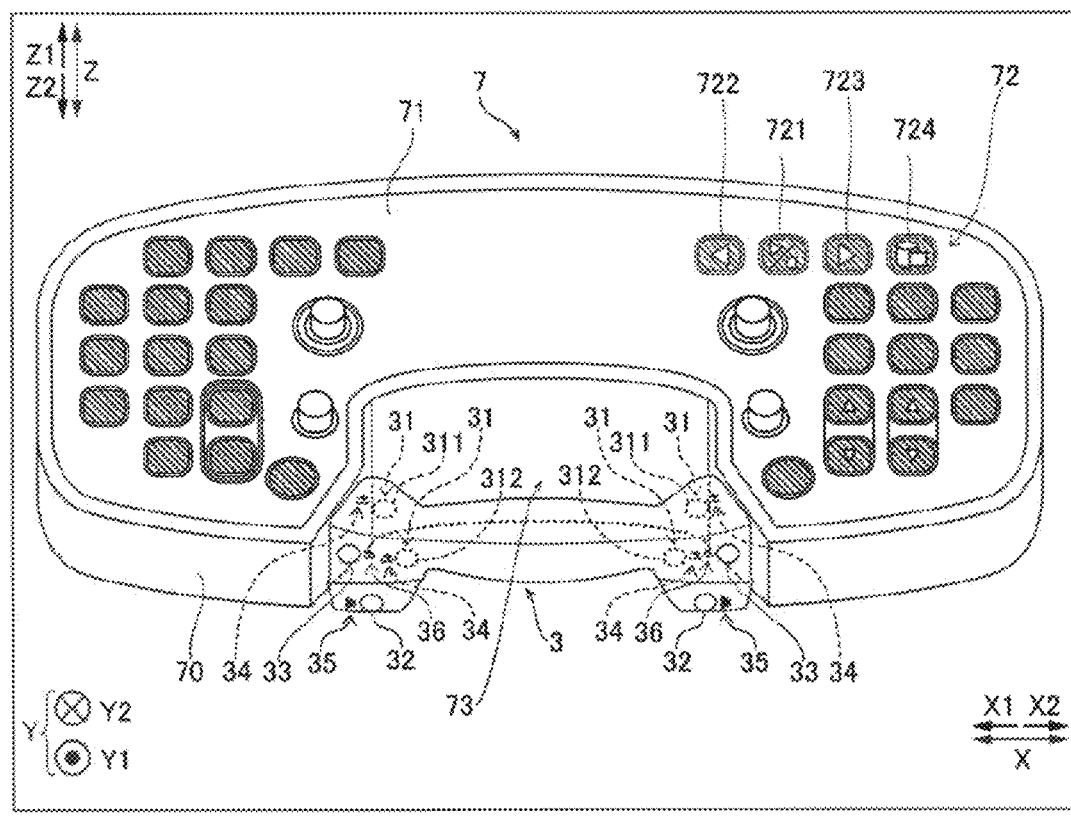
FIG. 4 is a schematic view showing an operation panel unit and a handle according to an embodiment of the present invention.

Next, with reference to FIG. 4, the operation panel unit 7 will be described. Note that the directions (X-direction, Y-direction, and Z-direction) shown in FIG. 4 are directions in the case where the posture of the X-ray fluoroscopic imaging apparatus 100 is in a horizontal state. The operation panel unit 7 includes a housing 70 and an operation surface plate 71. The operation surface plate 71 is held by the imaging unit 1 via the housing 70.

The housing 70 and the operation surface plate 71 have a cutout portion 73. At the open end portion of the cutout portion 73, a handle 3 is connected to the housing 70. The handle 3 is provided to face the imaging unit 1. In the example shown in FIG. 4, the cutout portion 73 of the housing 70 and the operation surface plate 71 is formed at a substantially central position in the direction (X-direction) along which the handle 3 extends.

The operation surface plate 71 is provided with a plurality of operation input portions 72 for receiving operation inputs for operating the imaging unit 1. The plurality of operation input portions 72 is used by the operator 201 to perform input operations at the time of executing the X-ray imaging and the X-ray fluoroscopy. The plurality of operation input portions 72 are used, for example, to move the top board 8, adjust the X-ray irradiation range, and the like. Furthermore, in this embodiment, the plurality of operation input portions 72 includes an image reproduction and stop button 721, an image backward button 722, an image forward button 723, and a fluoroscopic image saving button 724.

The image reproduction and stop button 721 is a button for instructing to display, reproduce, or stop reproducing an X-ray fluoroscopic moving image stored in the storage unit 5 (see FIG. 1) on the display unit 6. The image backward button 722 is a button for instructing to display a frame before one frame while an image is being displayed. When the leading frame is being displayed, the loop is performed to display the final frame. The image forward button 723 is a button for instructing to display a frame after one frame when an X-ray fluoroscopic image is being displayed. When the last frame is being displayed, the loop is performed to display the leading frame. The fluoroscopic image saving button 724 is a button for instructing the storage unit 5 to save an X-ray fluoroscopic image of a frame displayed on the display unit 6 as a still image.

Handle

Figure 5:
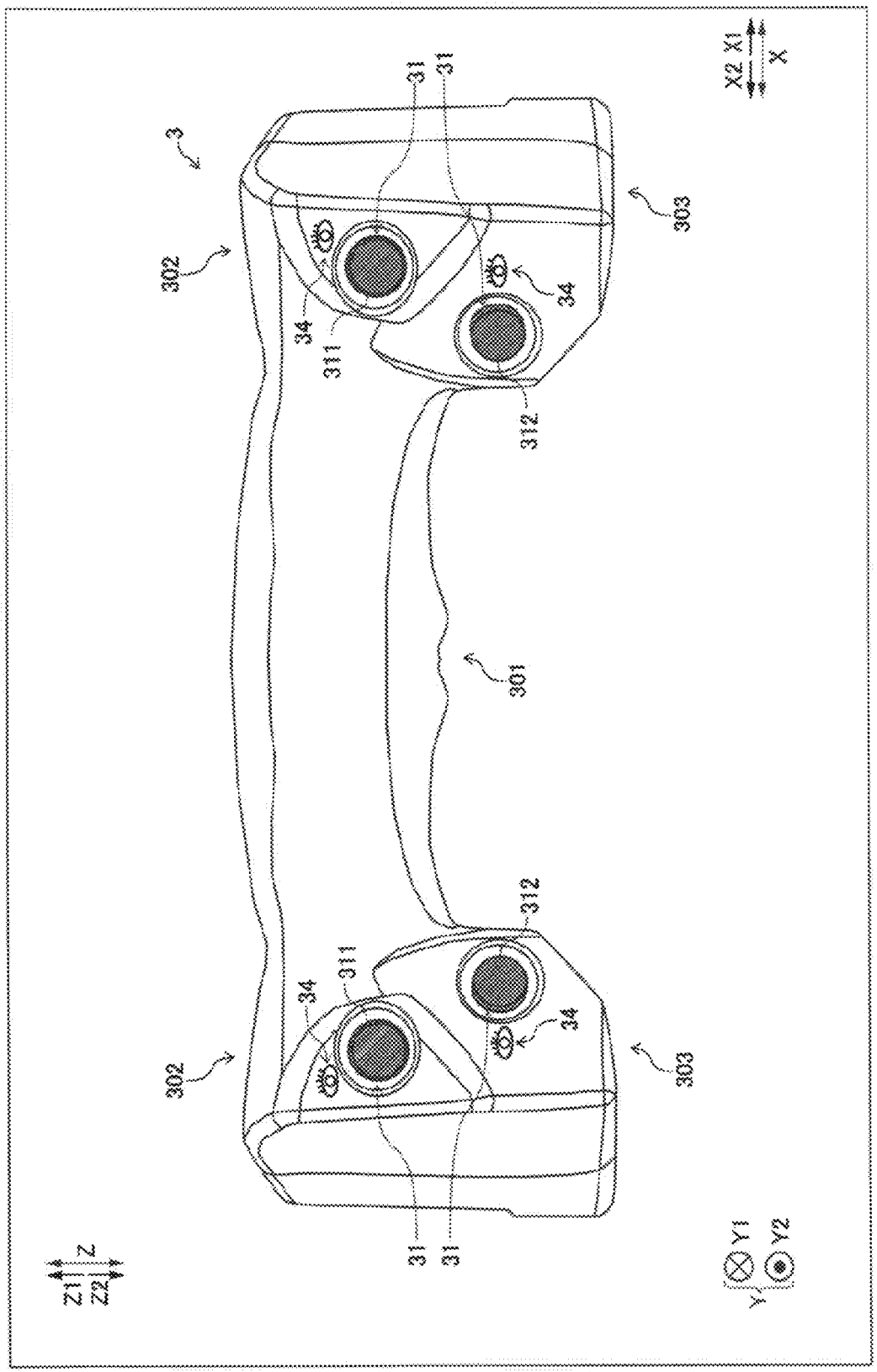
FIG. 5 is a schematic view showing an inner side configuration of the handle according to the embodiment of the present invention.
Figure 6:
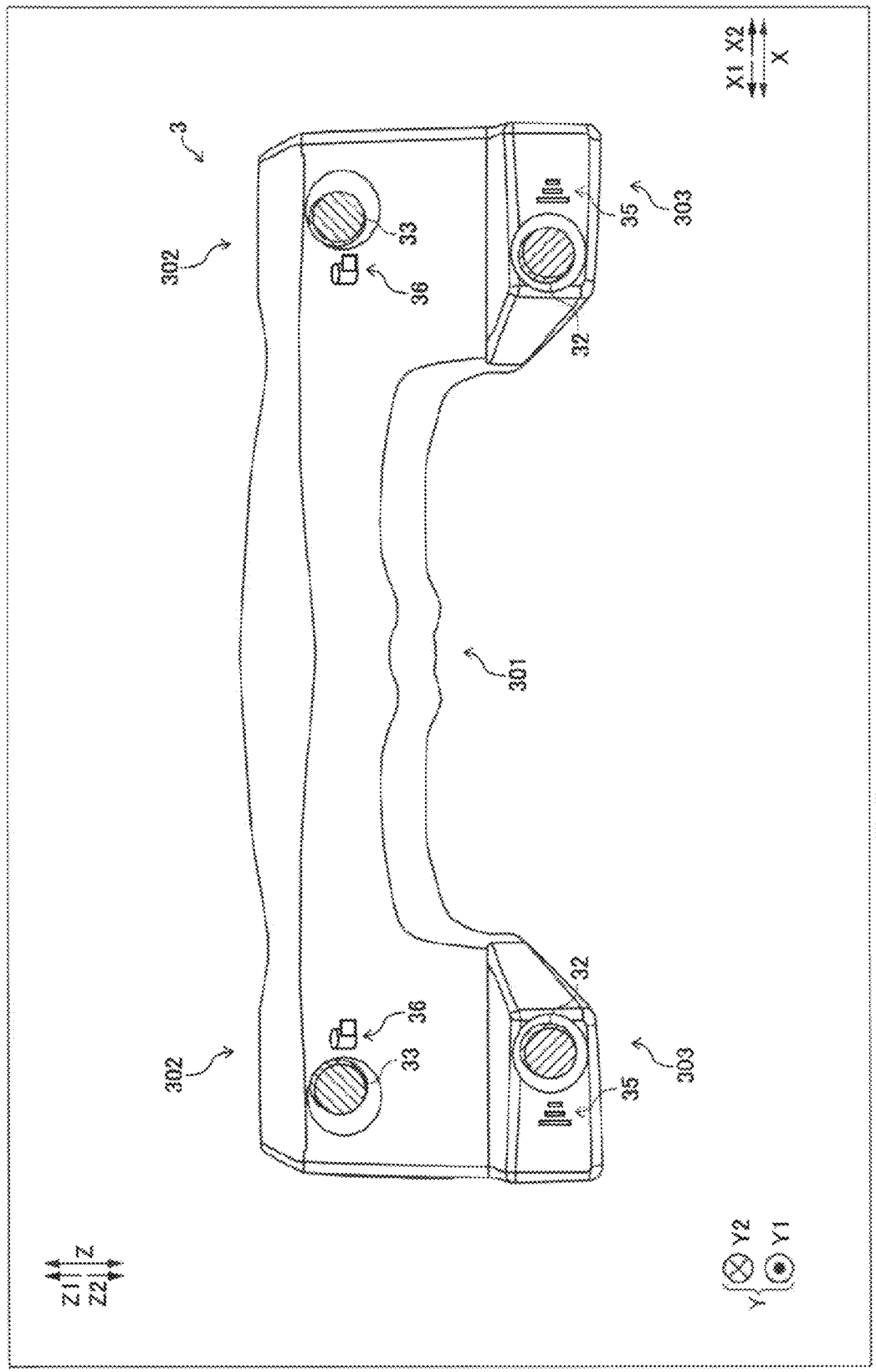
FIG. 6 is a schematic view showing an outer side configuration of the handle according to the embodiment of the present invention.

Next, the handle 3 will be described with reference to FIG. 5 and FIG. 6. Note that the directions (X-direction, Y-direction, and Z-direction) shown in FIG. 5 and FIG. 6 are directions when the posture of the X-ray fluoroscopic imaging apparatus 100 is in a horizontal state. As shown in FIG. 5 and FIG. 6, the handle 3 includes a gripping portion 301, end portions 302, and protruding portions 303 protruding from respective end portions 302. The gripping portion 301 extends substantially in parallel (X-direction) to the placement surface of the top board 8, and is served as a portion that the operator 201 grips when moving the imaging unit 1. The end portion 302 is an outer side portion of the gripping portion 301 in the handle 3. The protruding portion 303 is a portion that protrudes from the end portion 302 toward a side that intersects with the direction along which the handle 3 extend, i.e., in this embodiment, toward the placement surface side (the Z2-direction) of the top board 8.

The first fluoroscopic button 311 and the second fluoroscopic button 312 are arranged on the inner side surface of the handle 3 facing the imaging unit 1 (see FIG. 5), and the imaging button 32 is arranged on the outer side surface opposite to the inner side surface of the handle 3 (see FIG. 6). That is, the fluoroscopic buttons 31 and the imaging button 32 are arranged on different surfaces.

The arrangement of the buttons on the inner side surface (surface on the Y2-direction side) of the handle 3 facing the imaging unit 1 is shown in FIG. 5. On the inner side surface of the handle 3, fluoroscopic buttons 31 including the first fluoroscopic button 311 and the second fluoroscopic button 312 are provided. The fluoroscopic buttons 31 (the first fluoroscopic button 311 and the second fluoroscopic button 312) each are a button for performing an instruction to execute X-ray fluoroscopy, and are operated by the operator 201 in a state in which the operator 201 grips the handle 3 when executing X-ray fluoroscopy. Note that, in the vicinity of each fluoroscopic button 31, an icon 34 may be provided to indicate the function of the button.

The first fluoroscopic button 311 and the second fluoroscopic button 312 are each composed of a plurality of buttons, and are disposed near at least one end portion 302 (X1-direction) and the other end portion 302 (X2-direction) of the handle 3 in the direction along which the handle 3 extends. They are arranged symmetrically with respect to the center of the handle 3 in the direction along which the handle 3 extends (in the X-direction). In this embodiment, the first fluoroscopic buttons 311 and the second fluoroscopic buttons 312 are each composed of two buttons.

Specifically, one first fluoroscopic button 311 is arranged at one end portion 302 (X1-direction) of the handle 3 and one first fluoroscopic button 311 is arranged at the other end portion 302 (X2-direction) of the handle 3. Further, the first fluoroscopic button 311 arranged at one end portion 302 (X1-direction) and the first fluoroscopic button 311 arranged at in the other end portion 302 (X2-direction) are arranged at symmetrical positions. Note that the term "symmetrical" means symmetrical in the YZ-plane passing through the center of the handle 3 in the X-direction, or symmetrical with respect to a line extending in the Z-direction when viewed in the Y-direction and passing through the center of the handle 3 in the X-direction.

Furthermore, one second fluoroscopic button 312 is arranged at one protruding portion 303 (X1-direction) protruding in the Z2-direction and one second fluoroscopic button 312 is arranged at the other protruding portion 303 (X2-direction) protruding in the Z2-direction. Further, the second fluoroscopic button 312 arranged at one end protruding portion 303 (X1-direction) and the second fluoroscopic button 312 arranged at the other protruding portion 303 (X2-direction) are arranged at symmetrical positions. Note that the term "symmetrical" means symmetrical in the YZ-plane passing through the center of the handle 3 in the X-direction, or symmetrical with respect to a line extending in the Z-direction when viewed in the Y-direction and passing through the center of the handle 3 in the X-direction.

Further, the first fluoroscopic button 311 is arranged at the end portion 302 of the handle 3, and the second fluoroscopic button 312 is arranged at the protruding portion 303 protruding in a direction intersecting with the direction along which the handle 3 extends. That is, the first fluoroscopic button 311 and the second fluoroscopic button 312 are arranged offset from each other in a direction (Z-direction) intersecting with the direction along which the handle 3 extends (X-direction).

For example, at the time of gripping the handle 3 with the back of the hand up, when the handle 3 is located at a low position and the handle 3 is deeply gripped, the forefinger to the little finger are positioned on the Z2-direction side. On the other side, when the handle 3 is located at a high position and cannot be gripped deeply, the forefinger to the little finger are positioned on the Z1-direction side. Thus, the positions of fingers at the time of gripping the handle change depending on the position of the handle 3 and the way of gripping. In this embodiment, in order to cope with the change in the finger position as described above, the first fluoroscopic button 311 is arranged at the end portion 302 of the handle 3, and the second fluoroscopic button 312 is arranged at the protruding portion 303 on the Z2-direction side of the first fluoroscopic button 311. As described above, the second fluoroscopic button 312 is arranged at the protruding portion 303 located at the position apart from the gripping portion 301 in the Z2-direction, in a direction (Z-direction) intersecting with the direction (X-direction) along which the handle 3 extends.

In cases where the position of the handle 3 is low when the top board 8 is in a standing posture, etc., the position of the handle 3 may sometimes be located at a position away from the operator 201. In such a case, it is assumed that the handle 3 is gripped in an oblique direction with respect to the direction along which the handle 3 extends. When gripping the handle 3 obliquely with respect to the direction along which the handle 3 extends, the fingertip of the operator 201 is positioned closer to the center of the handle 3 than when gripping the handle 3 in a direction perpendicular to the direction along which the handle 3 extends. In this embodiment, the second fluoroscopic button 312 is arranged closer to the center of the handle 3 (closer to the gripping portion) than the first fluoroscopic button 311 in the direction (X-direction) along which the handle 3 extends.

Next, the arrangement of buttons on the outer side surface of the handle 3 (the surface on the Y1-direction side opposite to the surface facing the imaging unit 1) is shown in FIG. 6. On the outer side surface of the handle 3, an imaging button 32 and a fluoroscopic image saving button 33 are provided. The imaging button 32 is a button for performing an instruction to execute X-ray imaging, and is operated in a state in which the handle 3 is gripped when executing X-ray imaging. The fluoroscopic image saving button 33 is a button for performing an instruction to save the X-ray fluoroscopic image of the frame displayed on the display unit 6 as a still image in the storage unit 5 in the same manner as in the fluoroscopic image saving button 724 of the operation panel unit 7. Further, in the vicinity of the imaging button 32 and the fluoroscopic image saving button 33, an icon 35 and an icon 36 may be respectively provided to indicate the function of the button.

The imaging button 32 and the fluoroscopic image saving button 33 are each composed of a plurality of buttons, and are arranged near at least one end portion 302 (X1-direction) and the other end portion 302 (X2-direction) of the handle 3 in the direction along which the handle 3 extends. They are arranged symmetrically with respect to the center of the handle 3 in the direction along which the handle 3 extends.

Specifically, one imaging button 32 is arranged at the protruding portion 303 on one side (X1-direction) of the handle 3 and one imaging button 32 is arranged at the protruding portion 303 on the other side (X2-direction). Note that the imaging button 32 arranged at one end protruding portion 302 (X1-direction) and the imaging button 32 arranged at the other protruding portion 303 (X2-direction) are arranged at symmetrical positions. Further, one fluoroscopic image saving button 33 is arranged at one end portion 302 (X1-direction) of the handle 3 and one fluoroscopic image saving button 33 is arranged at the other end portion 302 (X2-direction) of the handle 3. Note that the fluoroscopic image saving button 33 arranged at one end portion 302 (X1-direction) and the fluoroscopic image saving button 33 arranged at the other end portion 302 (X2-direction) are arranged symmetrically with respect to the Z-axis.

Figure 7:
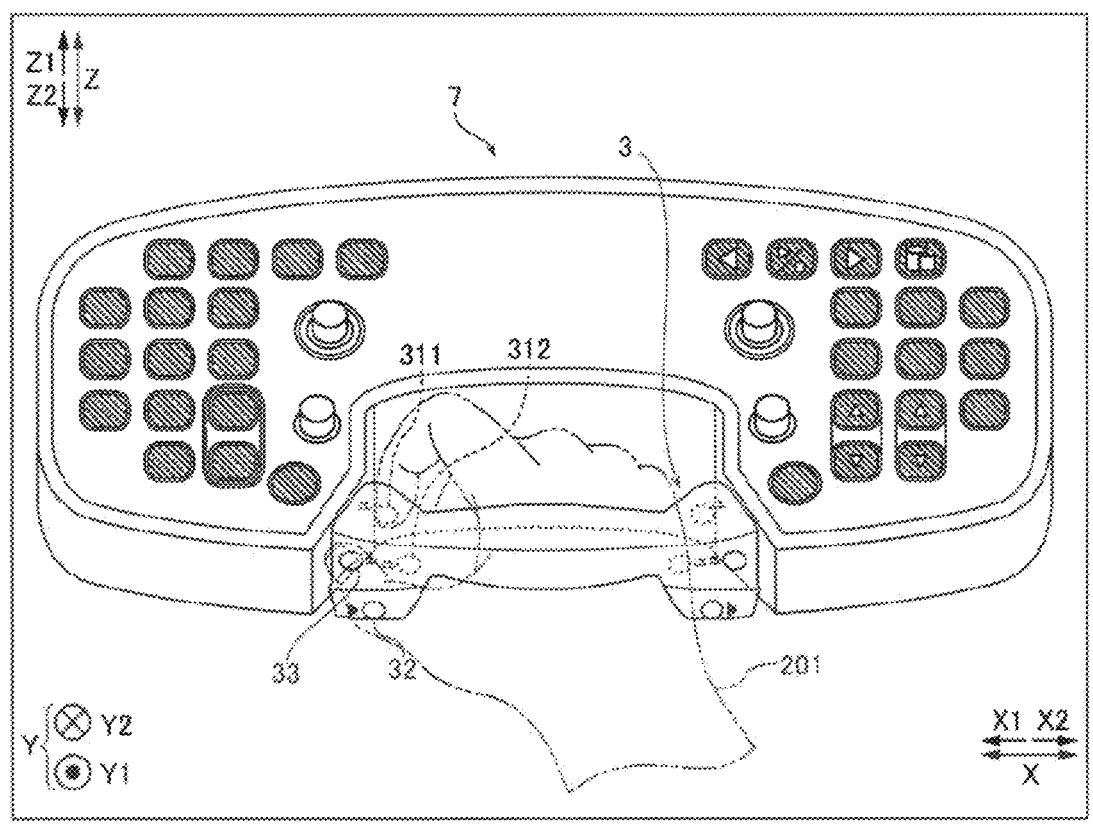
FIG. 7 is a schematic view showing an example of a gripping way of the handle according to the embodiment of the present invention.

An example of a way of gripping the handle 3 according to this embodiment is shown in FIG. 7. As shown in FIG. 7, in the state of gripping the handle 3 connected to the operation panel unit 7, the operator 201 can operate the fluoroscopic buttons 31 (the first fluoroscopic button 311 and the second fluoroscopic button 312) with the forefinger, and can operate the imaging button 32 and the fluoroscopic image saving button 33 with the thumb.

Effect of this Embodiment

In this embodiment, the following effects can be obtained. In this embodiment, on the one end portion 302 side (X1-direction) of the handle 3 and on the other end portion 302 side (X2-direction) thereof, the first fluoroscopic button 311 and the second fluoroscopic button 312 are respectively provided offset from each other in the direction (Z-direction) intersecting with the direction (X-direction) along which the handle 3 extends. This makes it possible to provide buttons (the first fluoroscopic button 311 and the second fluoroscopic button 312) at easy-to-operate positions in a plurality of gripping positions. As a result, it is possible to easily operate the buttons (the first fluoroscopic button 311 and the second fluoroscopic button 312) while performing the operation of moving the imaging unit 1 regardless of the position of the handle 3.

Also in this embodiment, the fluoroscopic button 31 includes the first fluoroscopic button 311 and the second fluoroscopic button 312 arranged offset from each other in a direction (Z-direction) intersecting with the direction (X-direction) along which the handle 3 extends on at least one end portion 302 (X1-direction) side in the direction along which the handle 3 extends. As a result, since the first fluoroscopic button 311 and the second fluoroscopic button 312 can cope with various ways of gripping the handle 3, the operability of the first fluoroscopic button 311 and the second fluoroscopic button 312 is improved.

In this embodiment, the first fluoroscopic buttons 311 and the second fluoroscopic buttons 312 are each composed of a plurality of buttons, and are arranged in the vicinity of at least one end portion 302 (X1-direction) and the other end portion 302 (X2-direction) in the direction along which the handle 3 extends. The imaging button 32 is composed of a plurality of buttons, and is arranged in the vicinity of at least one end portion 302 (X1-direction) and the other end portion 302 (X2-direction) in the direction along which the handle 3 extends. As a result, the fluoroscopic button 31 and the imaging button 32 are arranged in the vicinity of one end portion 302 (X1-direction) of the handle 3 and in the vicinity of the other end portion 302 (X2-direction) of the handle 3. Therefore, even with either the left hand or the right hand, the fluoroscopic button 31 and the imaging button 32 can be easily operated. With this, even when the handle 3 is gripped by either the left hand or the right hand, the fluoroscopic button 31 and the imaging button 32 can be easily operated.

Further, in this embodiment, the plurality of first fluoroscopic buttons 311 is arranged symmetrically with respect to the center of handle 3 in the direction (X-direction) along which the handle 3 extends. The plurality of second fluoroscopic buttons 312 is arranged symmetrically with respect to the center of handle 3 in the direction along which handle 3 extends. The plurality of imaging buttons 32 is arranged symmetrically with respect to the center of the handle 3 in the direction along which the handle 3 extends. With this, even when the handle 3 is gripped by either the left hand or the right hand, in the same manner as in the case where the handle 3 is gripped with the other hand, the first fluoroscopic button 311, the second fluoroscopic button 312, and the imaging button 32 can be operated.

Further, in this embodiment, the handle 3 is provided so as to face the imaging unit 1, the first fluoroscopic button 311 is arranged on the inner side surface of the handle 3 facing the imaging unit 1, the second fluoroscopic button 312 is arranged on the inner side surface of the handle 3 facing the imaging unit 1, and the imaging button 32 is arranged on the outer side surface opposite to the inner side surface of the handle 3. As a result, since the fluoroscopic button 31 and the imaging button 32 are arranged on different surface sides, an erroneous operation can be suppressed as compared with the case in which the fluoroscopic button 31 and the imaging button 32 are arranged on the same surface side.

Further, in this embodiment, the handle 3 includes the gripping portion 301 extending in a direction (X-direction) approximately parallel to the placement surface of the top board 8 and the protruding portion 303 protruding in a direction (Z-direction) extending in the direction (X-direction) along which the handle 3 extends from both end portions (end portion 302) outside the gripping portion 301. One of the first fluoroscopic button 311 and the second fluoroscopic button 312 is arranged at both end portions (end portions 302), and the other thereof is arranged at the protruding portions 303.

With this configuration, it is possible to arrange the fluoroscopic buttons 31 at positions separated from the gripping portion 301 in the direction (Z-direction) intersecting with the direction (X-direction) along which the handle 3 extends. Therefore, even when the tip position of the finger (for example, forefinger) changes according to the plurality of way of gripping the handle 3, in the direction (Z-direction) intersecting with the direction along which handle 3 extends, the first fluoroscopic button 311 and the second fluoroscopic button 312 can be provided at positions easy to operate with the respective fingers (for example, the index finger) (see FIG. 7). As a result, it is possible to further suppress the decrease in operability of the first fluoroscopic button 311 or the second fluoroscopic button 312 due to the way of gripping the handle 3.

Further, in this embodiment, the second fluoroscopic button 312 is arranged closer to the center of the handle 3 than the first fluoroscopic button 311 in the direction (X-direction) along which the handle 3 extends. Thereby, in addition to the direction (Z-direction) intersecting the direction along which handle 3 extends, in the direction (X-direction) along which the handle 3 extends, even when the tip position of the finger (for example, forefinger) changes according to the plurality of way of gripping the handle 3, the first fluoroscopic button 311 and the second fluoroscopic button 312 can be provided at positions easy to operate with the respective fingers (for example, the index finger) (see FIG. 7). As a result, it is possible to more effectively suppress the decrease in operability of the first fluoroscopic button 311 or the second fluoroscopic button 312 due to the way of gripping the handle 3.

Further, in this embodiment, a fluoroscopic image saving button 33, which is a button to perform an instruction to save an X-ray fluoroscopic image, is further provided. One of the fluoroscopic image saving button 33 and the imaging button 32 is arranged at both end portions (end portion 302), and the other thereof is arranged at the respective protruding portions 303. As a result, an X-ray fluoroscopic image can be stored after or during the X-ray fluoroscopy, so that the fluoroscopic image can be confirmed even after completion of the X-ray fluoroscopy.

Modified Embodiment

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the above embodiment, although an example in which the fluoroscopic image saving button 33 is provided on the handle 3 is shown, the present invention is not limited to this. In the present invention, only the fluoroscopic button and the imaging button may be provided without providing the fluoroscopic image saving button on the handle.

In the above embodiment, regarding the fluoroscopic button 31, an example is shown in which one first fluoroscopic button 311 and one second fluoroscopic button 312 are provided at one end portion 302 and the other end portion 302 of the handle 3, respectively, i.e., a total of four buttons, are provided, but the present invention is not limited to this. In the present invention, it may be configured such that the first fluoroscopic button and the second fluoroscopic button are provided on only one end portion or the other end portion of the handle. Alternatively, the number of fluoroscopic buttons may be further increased, and five or more fluoroscopic buttons may be provided on the handle.

In the above embodiment, an example is shown in which the fluoroscopic button 31 includes the first fluoroscopic button 311 and the second fluoroscopic button 312 arranged mutually offset in the direction (Z-direction) intersecting with the direction (X-direction) along which the handle 3 extends, but the present invention is not limited to this. In the present invention, it may be configured such that a plurality of imaging buttons is provided on either one end portion or the other end portion of the handle, and the plurality of imaging buttons may be arranged mutually offset in a direction intersecting with the direction along which the handle extends.

In the above embodiment, an example is shown in which the fluoroscopic button 31 and the imaging button 32 are provided on the handle 3, but the present invention is not limited thereto. In the present invention, it may be configured such that a plurality of fluoroscopic buttons is provided at either one end portion or the other end portion of the handle, and the imaging button is provided at a portion other than the handle such as the operation panel unit, alternatively, a plurality of imaging buttons is provided on either one end portion or the other end portion of the handle and a fluoroscopic button is provided on a portion other than the handle, such as, e.g., an operation panel unit.

In the above embodiment, an example is shown in which the fluoroscopic button 31 is arranged on the inner side surface of the handle 3 and the imaging button 32 and the fluoroscopic image saving button 33 are arranged on the outer side surface of the handle 3, but the present invention is not limited thereto. In the present invention, it may be configured such that the fluoroscopic buttons are arranged on the outer side surface of the handle and the imaging button and the fluoroscopic image saving button are arranged on the inside of the handle or that the fluoroscopic buttons are arranged on both sides of the outer side surface and the inner side surface of the handle.

In the above embodiment, an example is shown in which the fluoroscopic buttons 31, the imaging buttons 32, and the fluoroscopic image saving buttons 33 are each arranged symmetrically with respect to the center of the handle 3 in the direction along which the handle 3 extends, but the present invention is limited to this. In the present invention, it may be configured such that respective buttons are arranged asymmetrically with respect to the center of the handle.

In the above embodiment, an example is shown in which the handle 3 is provided with the protruding portion 303 and that the protruding portion 303 is provided with the second fluoroscopic button 312, but the present invention is not limited to this. In the present invention, it may be configured such that the handle is not provided with a protruding portion and both end portions of the handle are provided with a first fluoroscopic button and a second fluoroscopic button.

In the above embodiment, an example is shown in which the handle 3 is provided with the protruding portion 303 and that the protruding portion 303 is provided with the imaging button 32, but the present invention is not limited to this. In the present invention, it may be configured such that a fluoroscopic image saving button is provided at the protruding portion and an imaging button is provided at both end portions, or no protruding portion is provided at the handle and a fluoroscopic image saving button and an imaging button are provided at both end portions of the handle.

In the above embodiment, an example is shown in which the X-ray fluoroscopic image is stored by operating the fluoroscopic image saving buttons 33 and 724 after completion of the X-ray fluoroscopy, but the present invention is not limited to this. In the present invention, it may be configured such that the X-ray fluoroscopic image is stored in real time by operating the fluoroscopic image saving button during the X-ray fluoroscopy.

In the above embodiment, an example is shown in which the imaging unit moving mechanism 14 performs power assist when the operator 201 moves the imaging unit 1, but the present invention is not limited to this. In the present invention, the present invention may be applied to an X-ray fluoroscopic imaging apparatus that does not perform power assist when moving the imaging unit 1.

Further, in the above embodiment, an example is shown in which the handle 3 is connected to the operation panel unit 7, but the present invention is not limited to this. In the present invention, it is not required that the handle 3 is connected to the operation panel unit 7, and, for example, the handle 3 may be connected directly to the imaging unit 1.

Further, in the above embodiment, an example is shown in which the operation panel unit 7 is integrally provided to the imaging unit 1, but the present invention is not limited to this. In the present invention, it may be configured such that, for example, the operation panel unit is provided at the top board or the like.

In the above embodiment, an example is shown in which an icon for indicating the function of the button is provided in the vicinity of the button, but the present invention is not limited to this. In the present invention, the icon may not be provided in the vicinity of the button, or may be provided only on the outer side or the inner side of the handle.

Also, in the above embodiment, an example of the X-ray fluoroscopic imaging apparatus 100 is shown in which the top board 8 (the attitude of the apparatus) can execute the X-ray fluorescence and the X-ray imaging in the horizontal state and the standing state, but the present invention is not limited to this. In the present invention, the present invention may be applied to an X-ray fluoroscopic imaging apparatus that executes the X-ray fluorescence and the X-ray imaging only in one of the horizontal state and the standing state of the top board 8 (the posture of the apparatus).

Further, in the above embodiment, an example of the under-tube type X-ray fluoroscopic imaging apparatus 100 is shown in which the X-ray source 11 is located below the subject 200 and the X-ray detector 12 is located above the subject 200, but the present invention is not limited to this. In the present invention, the present invention may be applied to an over-tube type X-ray fluoroscopic imaging apparatus in which the X-ray source is located above the subject and the X-ray detector is located below the subject.

Aspects

It is understood by those skilled in the art that the above-described exemplary embodiments are specific examples of the following aspects.

Item 1

An X-ray fluoroscopic imaging apparatus comprising:
a top board configured to place a subject thereon;
an imaging unit including an X-ray source configured to emit X-rays toward the subject and an X-ray detector configured to detect X-rays emitted from the X-ray source and transmitted through the subject;
an image processing unit configured to generate an X-ray fluoroscopic image and an X-ray image based on a detection signal acquired by the imaging unit;
a handle configured to be gripped by an operator when relatively moving the imaging unit relative to the top board at least in a horizontal direction or vertical direction;
a fluoroscopic button configured to perform an instruction to execute X-ray fluoroscopy; and
an imaging button configured to perform an instruction to execute X-ray imaging with an X-ray dose more than an X-ray dose used when executing the X-ray fluoroscopy,
wherein at least one of the fluoroscopic button and the imaging button is configured to be able to perform an instruction operation in a state in which the operator grips the handle, and is composed of a plurality of buttons provided at least on one end portion side in a direction along which the handle extends and arranged offset in a direction intersecting with the direction along which the handle extends.

Item 2

The X-ray fluoroscopic imaging apparatus as recited in Item 1,
wherein the fluoroscopic button is composed of a first fluoroscopic button and a second fluoroscopic button arranged offset from each other in a direction intersecting with the direction along which the handle extends on at least one end portion side in the direction along which the handle extends.

Item 3

The X-ray fluoroscopic imaging apparatus as recited in claim 2,
wherein the first fluoroscopic button and the second fluoroscopic button are each composed of a plurality of buttons, and are arranged in the vicinity of at least one end portion and in the vicinity of the other end portion in the direction along which the handle extends, and
wherein the imaging button is composed of a plurality of buttons, and is arranged in the vicinity of at least one end portion and in the vicinity of the other end portion in the direction along which the handle extends.

Item 4

The X-ray fluoroscopic imaging apparatus as recited in Item 3,
wherein the plurality of the first fluoroscopic buttons is arranged symmetrically with respect to a center of the handle in the direction along which the handle extends,
wherein the plurality of the second fluoroscopic buttons is arranged symmetrically with respect to the center of the handle in the direction along which the handle extends, and
wherein the plurality of the imaging buttons is arranged symmetrically with respect to the center of the handle in the direction along which the handle extends.

Item 5

The X-ray fluoroscopic imaging apparatus as recited in Item 2,
wherein the handle is provided to face the imaging unit,
wherein the first fluoroscopic button is arranged on an inner side surface of the handle facing the imaging unit, wherein the second fluoroscopic button is arranged on the inner side surface of the handle facing the imaging unit, and wherein the imaging button is arranged on an outer side surface opposite to the inner side surface of the handle.

Item 6

The X-ray fluoroscopic imaging apparatus as recited in Item 2, wherein the handle includes a gripping portion extending in a direction approximately parallel to a placement surface of the top board and protruding portions protruding in a direction intersecting with the direction along which the handle extends from both end portions outside the gripping portion, and wherein one of the first fluoroscopic button and the second fluoroscopic button is arranged at both the end portions, and the other thereof is arranged at the protruding portions.

Item 7

The X-ray fluoroscopic imaging apparatus as recited in Item 6, wherein the second fluoroscopic button is arranged closer to a center of the handle than the first fluoroscopic button in the direction along which the handle extends.

Item 8

The X-ray fluoroscopic imaging apparatus as recited in Item 7, further comprising a fluoroscopic image saving button which is a button for performing an instruction to store the X-ray fluoroscopic image, wherein one of the fluoroscopic image saving button and the imaging button is arranged at both the end portions, and the other thereof is arranged at the protruding portions.

The invention claimed is:

1. An X-ray fluoroscopic imaging apparatus comprising:
a top board configured to place a subject thereon;
an imaging unit including an X-ray source configured to emit X-rays toward the subject and an X-ray detector configured to detect X-rays emitted from the X-ray source and transmitted through the subject;
an image processing unit configured to generate an X-ray fluoroscopic image and an X-ray image based on a detection signal acquired by the imaging unit;
a handle configured to be gripped by an operator when relatively moving the imaging unit relative to the top board at least in a horizontal direction or vertical direction;
a fluoroscopic button configured to perform an instruction to execute X-ray fluoroscopy; and
an imaging button configured to perform an instruction to execute X-ray imaging with an X-ray dose more than an X-ray dose used when executing the X-ray fluoroscopy,
wherein at least one of the fluoroscopic button and the imaging button is configured to perform an instruction operation in a state in which the operator grips the handle, and
wherein the fluoroscopic button is composed of a plurality of buttons provided at least on one end portion side in a direction along which the handle extends and arranged offset in a direction intersecting with the direction along which the handle extends.

2. The X-ray fluoroscopic imaging apparatus as recited in claim 1,
wherein the fluoroscopic button is composed of a first fluoroscopic button and a second fluoroscopic button arranged offset from each other in a direction intersecting with the direction along which the handle extends on at least one end portion side in the direction along which the handle extends.

3. The X-ray fluoroscopic imaging apparatus as recited in claim 2,
wherein the first fluoroscopic button and the second fluoroscopic button are each composed of a plurality of buttons, and are arranged in the vicinity of at least one end portion and in the vicinity of the other end portion in the direction along which the handle extends, and
wherein the imaging button is composed of a plurality of buttons, and is arranged in the vicinity of at least one end portion and in the vicinity of the other end portion in the direction along which the handle extends.

4. The X-ray fluoroscopic imaging apparatus as recited in claim 3,
wherein the plurality of the first fluoroscopic buttons is arranged symmetrically with respect to a center of the handle in the direction along which the handle extends,
wherein the plurality of the second fluoroscopic buttons is arranged symmetrically with respect to the center of the handle in the direction along which the handle extends, and
wherein the plurality of the imaging buttons is arranged symmetrically with respect to the center of the handle in the direction along which the handle extends.

5. The X-ray fluoroscopic imaging apparatus as recited in claim 2,
wherein the handle is provided to face the imaging unit,
wherein the first fluoroscopic button is arranged on an inner side surface of the handle facing the imaging unit,
wherein the second fluoroscopic button is arranged on the inner side surface of the handle facing the imaging unit, and
wherein the imaging button is arranged on an outer side surface opposite to the inner side surface of the handle.

6. The X-ray fluoroscopic imaging apparatus as recited in claim 2,
wherein the handle includes a gripping portion extending in a direction approximately parallel to a placement surface of the top board and protruding portions protruding in a direction intersecting with the direction along which the handle extends from both end portions outside the gripping portion, and
wherein one of the first fluoroscopic button and the second fluoroscopic button is arranged at both the end portions, and the other thereof is arranged at the protruding portions.

7. The X-ray fluoroscopic imaging apparatus as recited in claim 6,
wherein the second fluoroscopic button is arranged closer to a center of the handle than the first fluoroscopic button in the direction along which the handle extends.

8. The X-ray fluoroscopic imaging apparatus as recited in claim 7,
further comprising a fluoroscopic image saving button which is a button for performing an instruction to store the X-ray fluoroscopic image, wherein one of the fluoroscopic image saving button and the imaging button is arranged at both the end portions, and the other thereof is arranged at the protruding portions.

* * * * *